United States Patent [19]

Yokoshima et al.

[11] Patent Number: 4,536,588
[45] Date of Patent: Aug. 20, 1985

[54] ACETAL GLYCOL DIACRYLATES AND PROCESS FOR PRODUCING THEM

[75] Inventors: Minoru Yokoshima, Yamaguchi; Kazuyoshi Nawata, Onoda; Tetsuo Ohkubo, Ube; Hideaki Hattori, Yamaguchi, all of Japan

[73] Assignee: Nippon Kayaku Kabushiki Kaisha, Tokyo, Japan

[21] Appl. No.: 503,572

[22] Filed: Jun. 13, 1983

[30] Foreign Application Priority Data

Jun. 24, 1982 [JP] Japan ................. 57-107575

[51] Int. Cl.³ ............................ C07D 319/06
[52] U.S. Cl. ................... 549/374; 549/375
[58] Field of Search .................. 549/374, 375

[56] References Cited

U.S. PATENT DOCUMENTS 2,945,008  7/1960  Caldwell et al. ................. 549/335
3,376,315  4/1968  Burger et al. .................... 549/453
4,076,727  2/1978  Zey et al. ........................ 549/454

FOREIGN PATENT DOCUMENTS 1957621  5/1971  Fed. Rep. of Germany ...... 549/374

Primary Examiner—Ethel G. Love
Attorney, Agent, or Firm—Henry C. Nields

[57] ABSTRACT

Acetal glycol diacrylates of the formula:

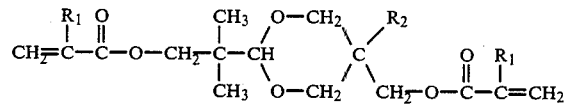

wherein $R_1$ represents H or $CH_3$ and $R_2$ represents $CH_3$, $C_2H_5$ or $C_3H_7$, and a process for producing them are provided.

4 Claims, No Drawings

ACETAL GLYCOL DIACRYLATES AND PROCESS FOR PRODUCING THEM

DETAILED DESCRIPTION OF THE INVENTION

The present invention relates to new acetal glycol diacrylates and a process for producing them.

Recently, ultraviolet curing printing inks and paints are gaining wide applications. Various acrylic esters are used as vehicles in these printing inks and paints.

After intensive investigations, the inventors have succeeded in producing new acetal glycol diacrylates having a high curing velocity and useful as vehicles in the ultraviolet curing printing inks and paints.

The present invention relates to new acetal glycol diacrylates of the following general formula [I]:

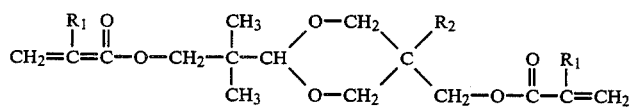

wherein $R_1$ represents H or $CH_3$ and $R_2$ represents $CH_3$, $C_2H_5$ or $C_3H_7$, preferably $C_2H_5$.

The new acetal glycol diacrylates [I] are produced by reacting an acetal glycol of the general formula [II]:

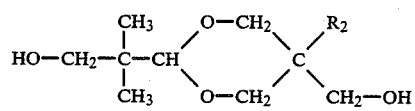

wherein $R_2$ represents $CH_3$, $CH_2H_5$ or $C_3H_7$, with acrylic acid or methacrylic acid at an elevated temperature. This reaction will be described in detail below. The acetal glycol of the general formula [II] is obtained by reacting 2,2-dimethyl-3-hydroxypropanol with a trimethylolalkane.

PREPARATION OF ACETAL GLYCOLS [II]

In the reaction of 2,2-dimethyl-3-hydroxypropanal with the trimethylolalkane, it is preferred to use a catalytically effective amount of a catalyst. The amount is 0.1 to 15 molar %, preferably 1 to 5 molar %, based on 2,2-dimethyl-3-hydroxypropanal. The useful catalysts are those known by those skilled in the chemical field of acetal reaction. As the useful catalysts, there may be mentioned acidic catalysts such as p-toluenesulfonic acid and sulfuric acid. The reaction of acetal glycol with the trimethylolalkane is carried out at a temperature of about 50° to 150° C., preferably 70° to 120° C., for a time sufficient for completing the reaction of these reactants charged. The amount of the trimethylolalkane charged is about 1 to 2 mol, preferably 1 mol, per mol of 2,2-dimethyl-3-hydroxypropanal.

If desired, an inert solvent such as toluene, benzene or cyclohexane may be used.

PREPARATION OF ACETAL GLYCOL DIACRYLATES [I]

The acetal glycol diacrylates [I] are prepared by reacting an acetal glycol [II] with acrylic acid, methacrylic acid or a mixture of them. The amount of acrylic or methacrylic acid is about 2 to 4 mol per mol of the acetal glycol [II] charged. It is desirable that 2 mol (astoichiometric amount) of acrylic or methacrylic acid is reacted with the reactive hydrogen of the hydroxyl group of the acetal glycol [II]. However, it is preferred in practice to use a slightly excess amount of the acid so as to perform the reaction completely. The reaction is carried out preferably in the presence of a polymerization inhibitor for minimizing or retarding the polymerization of the acrylic double bond. The polymerization inhibitors are those known by those skilled in the art. They are used in a concentration of 0.01 to 5 wt.% based on the mixture. As examples of the polymerization inhibitors, there may be mentioned hydroquinone, p-methoxyphenol, 2,4-dimethyl-6-t-butylphenol, phenothiazine, N-nitrosodiphenylamine and copper salts. The reaction is carried out generally at a temperature of about 50° to 130° C., preferably 65° to 90° C. for a time sufficient for completion of the esterification of the acetal glycol [II] with acrylic or methacrylic acid to form the acetal glycol diacrylate [I]. The reaction time varies depending on the scale of the batch, the respective reactants, catalysts and reaction conditions employed. The reaction is carried out in the presence of also an esterification catalyst in an amount of 0.1 to 15 molar %, preferably 1 to 6 molar %, based on acrylic or methacrylic acid used. Any of known esterification catalysts such as p-toluenesulfonic acid, methanesulfonic acid, phosphoric acid and sulfuric acid may be used. It is desirable to accelerate the removal of water formed during the esterification reaction by using an inert solvent such as toluene, benzene, cyclohexane or n-heptane.

The acetal glycol diacrylates [I] of the present invention may be separated from the solvent by washing with water or an aqueous alkali solution or by vacuum distillation, if necessary, prior to the use for industrial purposes. The acetal glycol diacrylates [I] are useful as vehicles to be incorporated in coating and ink compositions. They can be cured by exposure to radiations or by a thermal means. The radiation curing may be effected by corpuscular radiation such as ionizing radiation or electron beams or by chemical radiations such as ultraviolet radiation. In case the curing is effected by means of chemical radiations, various photosensitizers or photopolymerization initiators known in the art are used in general. The radiation curing techniques and thermosetting techniques known in the art may be employed. The acetal glycol diacrylates of the present invention may be used as vehicles either alone or in the form of a mixture with other monomers such as trimethylolpropane polyacrylate, pentaerythritol polyacrylate, pentaerythritol tetraacrylate or unsaturated group-containing resins, e.g., unsaturated polyesters, epoxy acrylate and urethane acrylate. The new acetal glycol diacrylates may be polymerized also by addition of an organic peroxide.

In a typical embodiment of the present invention, acrylic acid, the acetal glycol [II], catalyst, solvent and polymerization inhibitor are charged in a reactor. The mixture is heated until the esterification reaction is substantially completed. Then the acetal glycol diacrylate [I] is recovered by a conventional method.

The following acetal glycol synthesis examples and examples of the acetal glycol diacrylate production will further illustrate the present invention, in which parts are given by weight unless otherwise stated.

SYNTHESIS OF ACETAL GLYCOLS

Synthesis Example 1

250 parts of 2,2-dimethyl-3-hydroxypropanal, 328 parts of trimethylolpropane, 16.4 parts of p-toluenesulfonic acid, 520 parts of benzene and 130 parts of cyclohexane were charged in a 2-l reactor provided with a stirrer, thermostat, thermometer, condenser and separator. The mixture was heated. Water formed was distilled together with the solvent and condensed. Water alone was taken out of the system by means of the separator and the solvent was returned into the reactor. When 44 parts of water was formed, the reaction system was cooled. The reaction temperature was 70° to 85° C. The reaction mixture was dissolved in 2400 parts of benzene and 600 parts of cyclohexane and washed with 500 parts of a 20% aqueous common salt solution three times. The solvents were distilled off under reduced pressure to obtain 2,2-dimethyl-3-hydroxypropanal/trimethylolpropane condensate. The condensate was a white solid having a hydroxyl value of 515.1 and a melting point of 119° to 120.8° C.

SYNTHESIS EXAMPLE 2

102.1 parts of 2,2-dimethyl-4-hydroxypropanal, 120 parts of trimethylolethane, 5 parts of p-toluenesulfonic acid and 400 parts of toluene were charged in the same reactor as in Synthesis Example 1. The reaction was carried out in the same manner as in Example 1 until 18 parts of water was formed. The reaction temperature was 92° to 115° C. The solvent was distilled off under reduced pressure and the residue was filtered out and then purified to obtain 2,2-dimethyl-3-hydroxypropanal/trimethylolethane condensate. The condensate was a white solid having a hydroxyl value of 549.9 and melting point of 127° to 129.5° C.

PRODUCTION OF ACETAL GLYCOL DIACRYLATES

Example 1

436 parts of the acetal glycol of the following formula:

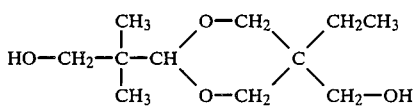

obtained in Synthesis Example 1, 345.8 parts of acrylic acid, 11.8 parts of sulfuric acid, 3 parts of hydroquinone, 400 parts of benzene and 100 parts of cyclohexane were charged in a 2 liter reactor provided with a stirrer, thermostat, condenser and separator. The mixture was heated. Water formed was distilled together with the solvent and condensed. Water alone was taken out of the system by means of the separator and the solvent was returned into the reactor. When 72 parts of water was formed, the reaction mixture was cooled. The reaction temperature was 82° to 90° C. The reaction mixture was dissolved in 800 parts of benzene and 200 parts of cyclohexane. After neutralization with a 20% aqueous sodium hydroxide solution, it was washed with 400 parts of a 20% aqueous common salt solution three times. The solvents were distilled off under reduced pressure to obtain 498.3 parts of a light yellow liquid having the following structural formula:

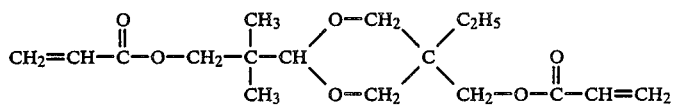

The product had the following properties:

| | |
|---|---|
| specific gravity (25° C.): | 1.083 |
| viscosity (25° C.): | 304.5 cps |
| saponification value: | 334.7 mg KOH/g |
| acid value: | 0.06 mg KOH/g |
| refractive index: | 1.4715 (20° C.) |
| elementary analysis: | C (%)   H (%) |
| | 63.01    8.10 |

The absorption of the resulting product was determined according to high resolution nuclear magnetic resonance (NMR) to obtain the following results:

| No. | Absorption frequency (Hz) |
|---|---|
| 1 | 2494.140 |
| 2 | 1970.703 |
| 3 | 1962.890 |
| 4 | 1958.984 |
| 5 | 1933.593 |
| 6 | 1929.687 |
| 7 | 1923.828 |
| 8 | 1615.234 |
| 9 | 1572.265 |
| 10 | 1193.359 |
| 11 | 1160.156 |
| 12 | 1128.906 |
| 13 | 1082.031 |
| 14 | 1072.265 |
| 15 | 1042.968 |
| 16 | 976.562 |
| 17 | 962.890 |
| 18 | 955.078 |
| 19 | 933.593 |
| 20 | 580.078 |
| 21 | 542.968 |
| 22 | 539.062 |
| 23 | 357.421 |
| 24 | 345.703 |
| 25 | 291.015 |
| 26 | 154.296 |
| 27 | 117.187 |
| 28 | 101.562 |
| 29 | 44.921 |
| 30 | 0.000 |

In the determination, tetramethylsilane was used as the internal reference and chloroform was used as the solvent. $H^1$, $C^{13}$—H coupling was effected and finally the identification results of $C^{13}$ D coupling are shown. In the above results, Nos. 10, 11 and 12 represent peaks of the solvent and No. 30 represents a peak of tetramethylsilane.

Example 2

436 parts of the acetal glycol of the following formula:

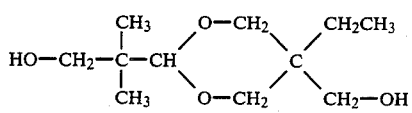

obtained in Synthesis Example 1, 412.8 parts of methacrylic acid, 2.20 parts of p-toluenesulfonic acid, 3.14 parts of hydroquinone and 500 parts of toluene were charged in the same reactor as in Example 1. The mixture was heated. Water formed was distilled together with the solvent and condensed. Water alone was taken out of the system by means of the separator and the solvent was returned into the reactor. When 72 parts of water was formed, the reaction mixture was cooled. The reaction temperature was 111° to 118° C. The reaction mixture was dissolved in 1000 parts of toluene. After neutralization with a 20% aqueous sodium hydroxide solution, it was washed with 400 parts of a 30% aqueous NaCl solution three times. The solvent was distilled off under reduced pressure to obtain 573 parts of a light yellow liquid having the following structural formula:

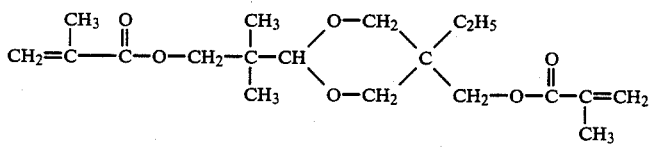

The product had the following properties:

| | |
|---|---|
| specific gravity (25° C.): | 1.060 |
| viscosity (25° C.): | 217.6 cps |
| saponification value: | 288.2 mg KOH/g |
| acid value: | 0.02 mg KOH/g |
| refractive index: | 1.4710 (20° C.) |
| elementary analysis: | C (%)   H (%) |
| | 65.03   8.92 |

NMR determination results

| No. | Absorption frequency (Hz) |
|---|---|
| 1 | 2511.718 |
| 2 | 2052.734 |
| 3 | 2048.828 |
| 4 | 1890.625 |
| 5 | 1880.859 |
| 6 | 1574.218 |
| 7 | 1416.015 |
| 8 | 1193.359 |
| 9 | 1160.156 |
| 10 | 1128.906 |
| 11 | 1083.984 |
| 12 | 1074.218 |
| 13 | 1044.921 |
| 14 | 978.515 |
| 15 | 957.031 |
| 16 | 582.031 |
| 17 | 544.921 |
| 18 | 539.062 |
| 19 | 488.281 |
| 20 | 359.375 |
| 21 | 347.656 |
| 22 | 292.968 |
| 23 | 275.390 |
| 24 | 251.953 |
| 25 | 117.187 |
| 26 | 101.562 |
| 27 | 42.968 |

In the above results, Nos. 8, 9 and 10 represent peaks of the solvent.

Example 3

408.3 parts of the acetal glycol of the following formula:

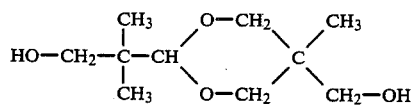

obtained in Synthesis Example 2, 345.8 parts of acrylic acid, 20 parts of p-toluenesulfonic acid, 2 parts of hydroquinone, 640 parts of benzene and 160 parts of cyclohexane were charged in the same reactor as in Example 1. The mixture was heated. Water formed was distilled together with the solvent and condensed. Water alone was taken out of the system by means of the separator and the solvent was returned into the reactor. When 72 parts of water was formed, the reaction mixture was cooled. The reaction temperature was 81° to 86° C. The reaction mixture was dissolved in 560 parts of benzene and 140 parts of cyclohexane. After neutralization with a 20% aqueous sodium hydroxide solution, it was washed with 400 parts of a 20% aqueous NaCl solution three times. The solvent was distilled off under reduced pressure to obtain 528 parts of a light yellow liquid having the following structural formula:

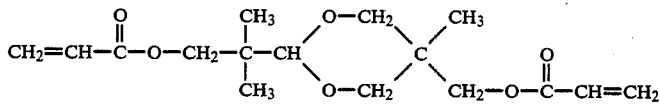

The product had the following properties:

| | |
|---|---|
| specific gravity (25° C.): | 1.0920 |
| viscosity (25° C.): | 285.7 cps |
| saponification value: | 357.9 mg KOH/g |
| refractive index: | 1.4695 |
| elementary analysis: | C (%)   H (%) |
| | 61.31   7.76 |

NMR determination results

| No. | Absorption frequency (Hz) |
|---|---|
| 1 | 3724.609 |
| 2 | 2769.531 |
| 3 | 2494.140 |
| 4 | 2400.390 |
| 5 | 2234.375 |
| 6 | 1970.703 |
| 7 | 1962.890 |
| 8 | 1953.984 |
| 9 | 1927.734 |
| 10 | 1921.875 |
| 11 | 1677.734 |
| 12 | 1611.328 |
| 13 | 1568.359 |
| 14 | 1191.406 |
| 15 | 1158.203 |
| 16 | 1126.953 |
| 17 | 1099.609 |
| 18 | 1093.750 |
| 19 | 1041.015 |
| 20 | 1011.718 |
| 21 | 998.046 |
| 22 | 988.281 |
| 23 | 853.515 |
| 24 | 621.093 |
| 25 | 585.937 |
| 26 | 578.125 |
| 27 | 509.765 |
| 28 | 505.859 |
| 29 | 503.906 |
| 30 | 289.062 |
| 31 | 277.343 |
| 32 | 269.531 |
| 33 | 251.953 |

In the above results, Nos. 14, 15 and 16 represent peaks of the solvent.

APPLICATION EXAMPLES 1 TO 3 AND COMPARATIVE EXAMPLES 1 TO 3

50 parts of epoxy acrylate resin [obtained by esterifying Epikote 828 (bisphenol type epoxy resin of Shell International Chemicals Corp.) with acrylic acid] and 5 parts of Irgacure 651 (a product of Ciba-Geigy Ltd.) as a photosensitizer were added to 50 parts of the new acetal glycol diacrylate obtained in the above Examples 1, 2 or 3. The mixture was applied to a steel panel and cured by ultraviolet rays using a high pressure mercury lamp (a product of Toshiba Co., Ltd.; 2 kw). The results are shown in Table 1. For comparison, curing results of the same composition as above except that the acetal glycol diacrylate was replaced with neopentyl glycol diacrylate (NPGDA; a product of Nippon Kayaku Co., Ltd.), 1,6-hexanediol diacrylate (HDDA; a product of Nippon Kayaku Co., Ltd.) or hydroxypivalic acid/neopentyl glycol diacrylate (MANDA; a product of Nippon Kayaku Co., Ltd.) are also shown.

TABLE 1

| | No. | Acrylate monomer | Curing time |
|---|---|---|---|
| Application Example | 1 | obtained in Example 1 | 2 |
| Application Example | 2 | obtained in Example 2 | 7 |
| Application Example | 3 | obtained in Example 3 | 2 |
| Comparative Example | 1 | NPGDA | 6 |
| Comparative Example | 2 | HDDA | 6 |
| Comparative Example | 3 | MANDA | 9 |

Note
1 Number of passing times of the sample at a rate of 18 m/min 8 cm below the high pressure mercury lamp until the tack-free time.

What is claimed is:

1. Acetal glycol diacrylates represented by the following general formula [I]:

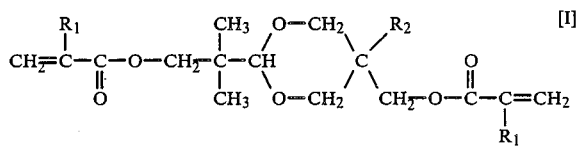

wherein $R_1$ represents H or $CH_3$ and $R_2$ represents $CH_3$, $C_2H_5$ or $C_3H_7$.

2. Acetal glycol diacrylates according to claim 1 wherein $R_1$ is H.

3. Acetal glycol diacrylates according to claim 1 wherein $R_2$ is $CH_3$.

4. Acetal glycol diacrylates according to claim 1 wherein $R_2$ is $C_2H_5$.

* * * * *